US010101253B2

(12) United States Patent
Arai

(10) Patent No.: US 10,101,253 B2
(45) Date of Patent: Oct. 16, 2018

(54) METHOD OF AND APPARATUS FOR DETECTING A CRACK IN A PAIR OF PIEZOELECTRIC ELEMENTS BASED ON TRANSFER FUNCTION

(71) Applicant: NHK SPRING CO., LTD., Yokohama-shi, Kanagawa (JP)

(72) Inventor: Mikio Arai, Kanagawa (JP)

(73) Assignee: NHK Spring Co., Ltd., Kanagawa (JP)

( * ) Notice: Subject to any disclaimer, the term of this patent is extended or adjusted under 35 U.S.C. 154(b) by 0 days.

(21) Appl. No.: 15/448,843

(22) Filed: Mar. 3, 2017

(65) Prior Publication Data

US 2017/0268973 A1 Sep. 21, 2017

(30) Foreign Application Priority Data

Mar. 16, 2016 (JP) .................................. 2016-52714

(51) Int. Cl.
| | | |
|---|---|---|
| *G01N 3/32* | (2006.01) | |
| *G11B 5/55* | (2006.01) | |
| *G11B 20/18* | (2006.01) | |
| *G11B 19/08* | (2006.01) | |
| *G11B 5/48* | (2006.01) | |

(52) U.S. Cl.
CPC ....... *G01N 3/32* (2013.01); *G01N 2203/0051* (2013.01); *G01N 2203/0064* (2013.01); *G11B 5/483* (2015.09); *G11B 5/4826* (2013.01); *G11B 5/4873* (2013.01); *G11B 5/5552* (2013.01); *G11B 19/08* (2013.01); *G11B 20/1816* (2013.01)

(58) Field of Classification Search
CPC ... G11B 5/4873; G11B 5/4826; G11B 5/5552; G11B 5/483; G11B 20/1816; G11B 19/048; G01N 19/08; G01N 3/32; G01N 2203/0064; G01N 2203/0051
USPC ........ 324/727, 537, 555; 360/294.4; 73/799, 73/808
See application file for complete search history.

(56) References Cited

U.S. PATENT DOCUMENTS

| | | | | |
|---|---|---|---|---|
| 6,861,854 | B1 * | 3/2005 | Guo ....................... | G11B 27/36 324/727 |
| 8,248,083 | B2 * | 8/2012 | Inoue ................... | G11B 5/5552 324/537 |

(Continued)

FOREIGN PATENT DOCUMENTS

| | | |
|---|---|---|
| JP | 06-003305 | 1/1994 |
| JP | 2002-050140 | 2/2002 |
| JP | 2002-367306 | 12/2002 |

*Primary Examiner* — Jonathan Dunlap
(74) *Attorney, Agent, or Firm* — Norris McLaughlin & Marcus, P.A.

(57) ABSTRACT

The present invention provides a method of surely detecting a crack in piezoelectric elements regardless of size of the crack. The method includes applying voltage to a first piezoelectric element of a pair of piezoelectric elements to cause deformation in the first piezoelectric element, forcibly deforming a second piezoelectric element of the pair of the piezoelectric elements to generate voltage from the second piezoelectric element according to the deformation of the first piezoelectric element, finding a transfer function of the pair of the piezoelectric elements based on values of the applied voltage and the generated voltage, and detecting presence or absence of a crack in the pair of the piezoelectric elements based on an objective value obtained from the found transfer function.

6 Claims, 16 Drawing Sheets

(56) References Cited

U.S. PATENT DOCUMENTS

| | | | | |
|---|---|---|---|---|
| 8,890,553 | B2* | 11/2014 | Furuta | G01R 29/22 |
| | | | | 324/525 |
| 9,042,056 | B2* | 5/2015 | Hanya | G11B 5/4826 |
| | | | | 360/294.4 |
| 2001/0043443 | A1 | 11/2001 | Okamoto et al. | |
| 2003/0076121 | A1* | 4/2003 | Guo | G11B 20/1816 |
| | | | | 324/727 |
| 2008/0106823 | A1* | 5/2008 | Yao | G11B 5/4826 |
| | | | | 360/294.4 |
| 2008/0144225 | A1* | 6/2008 | Yao | G11B 5/4826 |
| | | | | 360/294.4 |
| 2010/0264934 | A1* | 10/2010 | Inoue | G11B 5/5552 |
| | | | | 324/537 |
| 2011/0079351 | A1* | 4/2011 | Furuta | C09J 5/00 |
| | | | | 156/275.5 |
| 2012/0146671 | A1* | 6/2012 | Furuta | G01N 27/02 |
| | | | | 324/727 |
| 2013/0301164 | A1* | 11/2013 | Nishida | G11B 5/48 |
| | | | | 360/244.7 |
| 2014/0085754 | A1* | 3/2014 | Hanya | G11B 5/4826 |
| | | | | 360/244.5 |
| 2014/0368955 | A1* | 12/2014 | Nishida | G11B 5/48 |
| | | | | 360/244.7 |
| 2015/0219551 | A1* | 8/2015 | Greegor | G01M 5/005 |
| | | | | 73/810 |

* cited by examiner

FIG.4

| SAMPLE NUMBER | CAPACITANCE | | DIELECTRIC TANGENT | |
|---|---|---|---|---|
| | BEFORE | AFTER | BEFORE | AFTER |
| 1 | 543.7 | 546.9 | 0.033 | 0.036 |
| 2 | 536.1 | 537.3 | 0.034 | 0.034 |
| 3 | 536.4 | 532.4 | 0.034 | 0.037 |
| 4 | 538.6 | 536.4 | 0.037 | 0.039 |
| 5 | 537.7 | 538.2 | 0.036 | 0.036 |

10~15kHz

20~25kHz

35~38kHz

55~65kHz

65~80kHz

75~80kHz

10~15kHz

20~25kHz

35~38kHz

55~65kHz

65~80kHz

75~80kHz

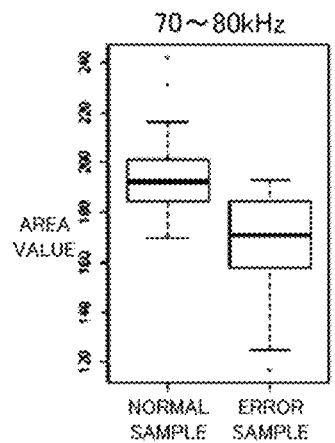 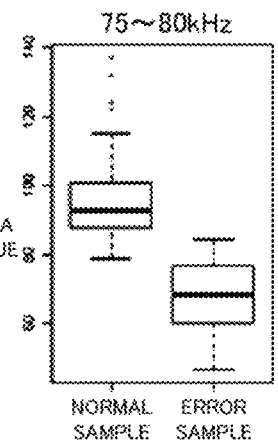 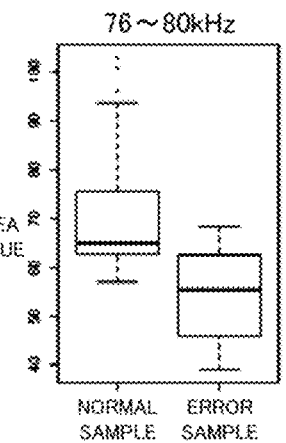
FIG.12A 70~80kHz    FIG.12B 75~80kHz    FIG.12C 76~80kHz
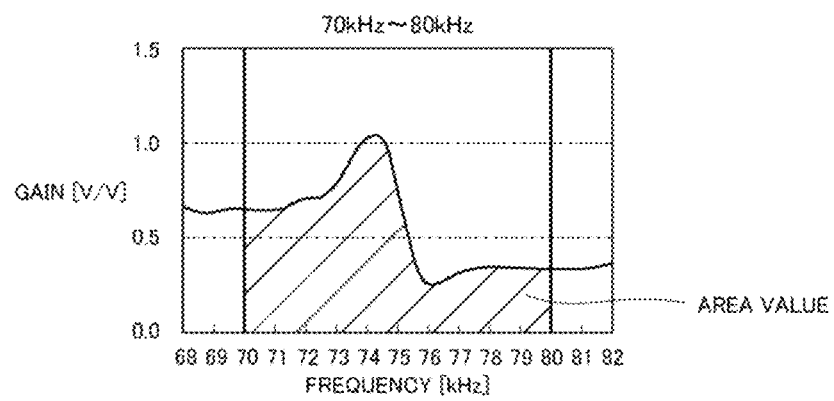
FIG.13

10~15kHz

20~25kHz

35~38kHz

55~65kHz

65~80kHz

75~80kHz

FIG.16
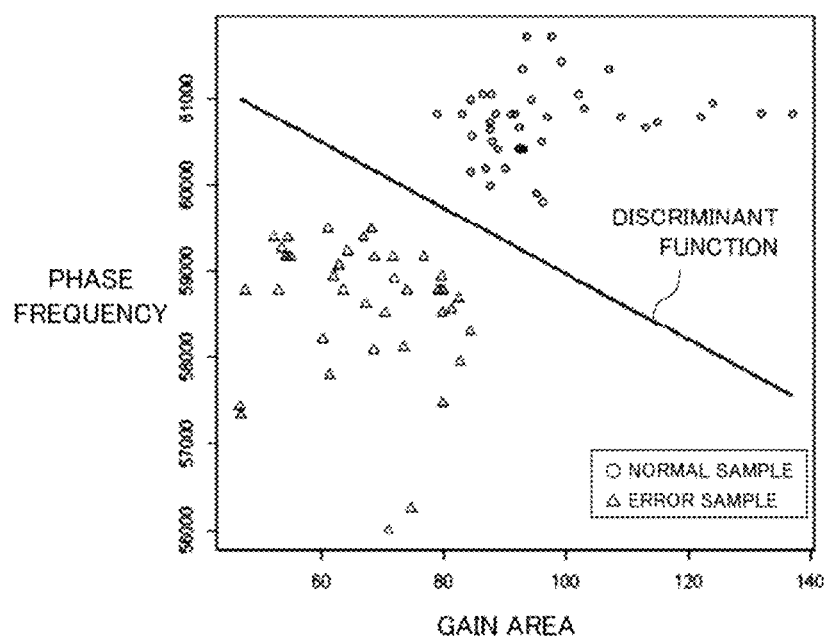
FIG.17
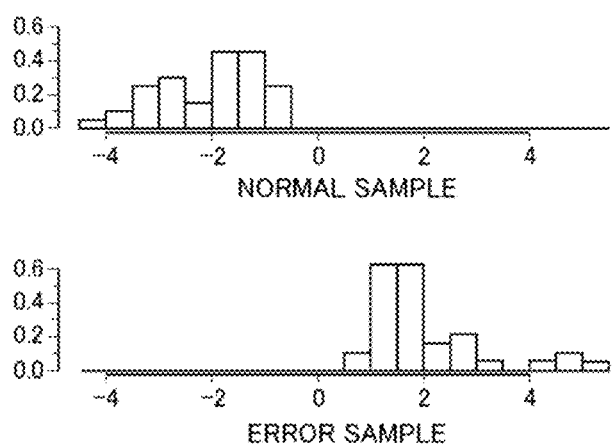
FIG.18
|  | NORMAL PRODUCT | ERROR PRODUCT |
|---|---|---|
| NORMAL SAMPLE | 40 |  |
| ERROR SAMPLE |  | 38 |

METHOD OF AND APPARATUS FOR DETECTING A CRACK IN A PAIR OF PIEZOELECTRIC ELEMENTS BASED ON TRANSFER FUNCTION

BACKGROUND OF THE INVENTION

1. Field of the Invention

The present invention relates to a method of and an apparatus for detecting a crack in a pair of piezoelectric elements used for a piezoelectric actuator or the like.

2. Description of the Related Art

There is a dual-actuator system as a technique to realize high density of a hard disk drive (HDD) as disclosed in JP2002-50140A. The dual-actuator system has a head suspension with a piezoelectric actuator in addition to a voice coil motor.

The voice coil motor drives a carriage to which the head suspension is attached to turn the head suspension. The piezoelectric actuator includes piezoelectric elements being arranged at an intermediate portion between a base plate and a load beam or at a head portion and being deformable according to voltage applied thereto to minutely drive the head portion in a sway direction. The dual-actuator system, therefore, precisely positions a magnetic head on the head portion.

The head suspension used in the dual-actuator system needs to be thinned according to downsizing of the HDD. Accordingly, the piezoelectric element used for the piezoelectric actuator also needs to be thinned.

The thinned piezoelectric element is likely to cause micro cracks by external force received, for example, at the time of production of the piezoelectric element or assembly of the same to the head suspension. A cracked piezoelectric element is concerned about reduction of long-term reliability and must be discarded as a defective.

A micro crack, however, is hard to be found from appearance using a stereoscopic microscope in general. The hardness is promoted by electrodes formed by gold plating, platinum plating or the like on the surfaces of the piezoelectric element.

Further, such a micro crack is hard to be found by measuring electric characteristics, either. Namely, a piezoelectric element is subjected to a performance test at which, for example, capacitance is measured after assembled into a head suspension. The micro crack, however, do not cause a change in the capacitance.

On the other hand, there are methods of detecting a crack of a piezoelectric element in which one conducts comparison between patterns in frequency characteristics of impedances and/or phases and the other uses optical transparency of a piezoelectric element as disclosed in, for example, JPH06-003305A and JP2002-367306A.

These methods, however, hardly determine presence or absence of a crack or are hardly applied for practical purposes. As a result, these methods do not surely detect a micro crack.

SUMMARY OF THE INVENTION

An object of the present invention is to provide a method of and an apparatus for surely detecting a crack in piezoelectric elements regardless of size of the crack.

In order to accomplish the object, a first aspect of the present invention provides a method of detecting a crack in piezoelectric elements. The method includes applying voltage to a first piezoelectric element of a pair of piezoelectric elements that are united with each other and are deformable integrally, to cause deformation in the first piezoelectric element, forcibly deforming a second piezoelectric element of the pair of the piezoelectric elements according to the deformation of the first piezoelectric element, to generate voltage from the second piezoelectric element, finding a transfer function of the pair of the piezoelectric elements based on a value of the applied voltage to the first piezoelectric element and a value of the generated voltage from the second piezoelectric element, and detecting presence or absence of a crack in one or both of the pair of the piezoelectric elements based on an objective value obtained from the found transfer function.

A second aspect of the present invention provides an apparatus for detecting a crack in piezoelectric elements. The apparatus includes a power source electrically connected to a first piezoelectric element of a pair of piezoelectric elements that are united with each other and are deformable integrally to apply voltage to the first piezoelectric element and cause the first piezoelectric element to deform, a voltage measuring device electrically connected to a second piezoelectric element of the pair of the piezoelectric elements to measure voltage generated from the second piezoelectric element that is forcibly deformed according to the deformation of the first piezoelectric element, and a crack detector electrically connected to the power source and the voltage measuring device whereby the crack detector obtains from the power source a value of the applied voltage to the first piezoelectric element and from the voltage measuring device a value of the measured voltage, finds a transfer function of the pair of the piezoelectric elements based on the values of the applied voltage and the measured voltage, and detects presence or absence of a crack in one or both of the pair of the piezoelectric elements based on an objective value obtained from the found transfer function.

According to the first aspect, voltage is applied not to both the pair of the piezoelectric elements but to only the first piezoelectric element of the pair of the piezoelectric elements to generate voltage from the second piezoelectric element thereof. Then, the transfer function is found using the values of the applied voltage and the generated voltage. The found transfer function provides the objective value that enables a crack to be surely detected even if the crack is a micro crack. Namely, the first aspect surely detects a crack in one or both of the pair of the piezoelectric element regardless of size of the crack.

According to the second aspect, the apparatus easily and simply realizes the method of the first aspect.

BRIEF DESCRIPTION OF THE DRAWINGS

FIG. 4 is a table of measurement results of electric characteristics of piezoelectric elements before and after crack generation;

FIGS. 12A to 12C are box-and-whisker plots illustrating distributions of area values in respective frequency ranges set on the gain characteristics of the transfer functions of the error samples and the normal samples of FIG. 9;

FIG. 13 is an explanatory view for finding an area value used in FIGS. 12A to 12C;

FIG. 16 is a graph illustrating the result of the discriminant analysis that completely discriminates between the error samples and the normal samples of FIG. 9;

FIG. 17 is a graph classifying the error and normal samples at values obtained by a discriminant in the discriminant analysis of FIG. 16;

FIG. 18 is a table illustrating discriminant results of the error and normal samples determined as error and normal products in the discriminant analysis of FIG. 16;

DETAILED DESCRIPTION OF EMBODIMENTS

Figure 1:
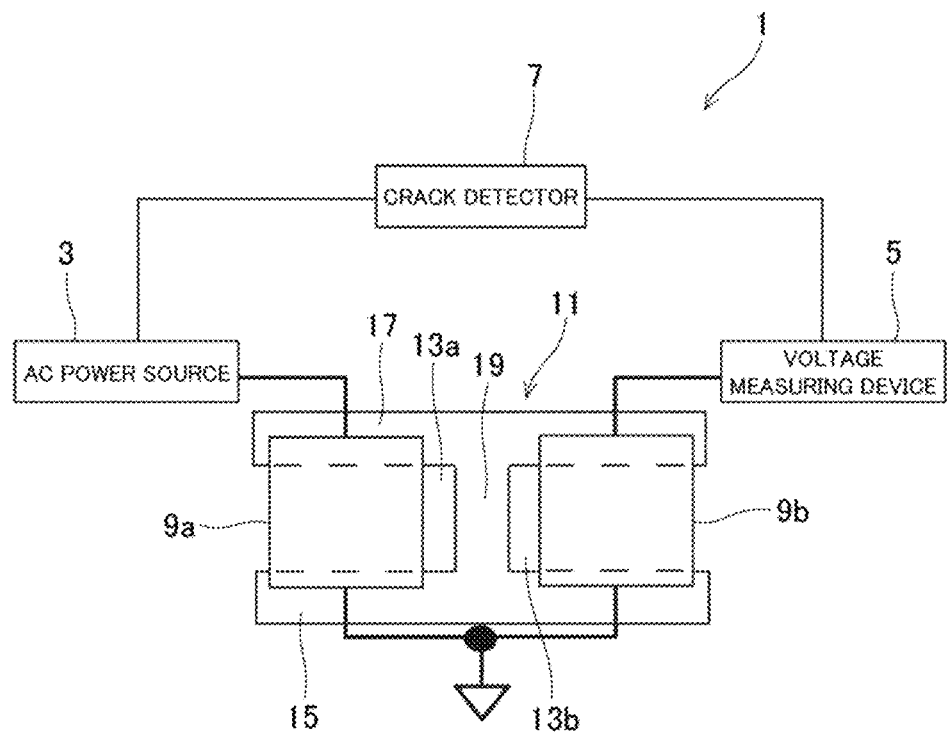
FIG. 1 is a general view schematically illustrating a crack detecting apparatus for piezoelectric elements according to an embodiment of the present invention.

An embodiment according to the present invention will be explained. The embodiment provides a crack detecting method and a crack detecting apparatus as a method of and an apparatus for surely detecting a crack in piezoelectric elements regardless of size of the crack.

For this, the crack detecting method applies voltage to a first piezoelectric element of a pair of piezoelectric elements to cause deformation in the first piezoelectric element, generates voltage from a second piezoelectric element of the pair of the piezoelectric elements forcibly deformed according to the deformation of the first piezoelectric element, finds a transfer function of the pair of the piezoelectric elements based on values of the applied voltage and the generated voltage, and detects presence or absence of a crack in one or both of the pair of the piezoelectric elements based on an objective value obtained from the found transfer function.

The pair of the piezoelectric elements may have respective first ends attached to a stationary member and respective second ends attached to a movable member. In this case, the applying step displaces the movable member according to the first piezoelectric element and the deforming step forcibly deforms the second piezoelectric element by the displaced movable member to generate the voltage.

The detecting step may compare the objective value with a reference value or evaluates the objective value using a discriminant, thereby to detect presence or absence of a crack in one or both of the pair of the piezoelectric elements.

The reference value may be a value obtained from a transfer function found in advance based on at least one error sample of a pair of piezoelectric elements in which one or both first and second piezoelectric elements are cracked or at least one normal sample of a pair of piezoelectric elements in which both first and second piezoelectric elements are not cracked.

The discriminant may be a discriminant function obtained by discriminant analyses conducted to error values and normal values, the error values being values obtained from transfer functions found in advance based on plural error samples each being a pair of piezoelectric elements in which one or both first and second piezoelectric elements are cracked and the normal values being values obtained from transfer functions found in advance based on plural normal samples each being a pair of piezoelectric elements in which both first and second piezoelectric elements are not cracked.

The transfer function may be a frequency transfer function. In this case, the objective value may be a peak value, an area value or a frequency value of a peak in a waveform of a gain characteristic or a phase characteristic of the frequency transfer function, said peak being within a range of the waveform defined so as to include said peak and not to include adjacent peaks of said peak.

The crack detecting apparatus used for the crack detecting method may include a power source electrically connected to the first piezoelectric element of the pair of the piezoelectric elements that are united with each other and are deformable integrally, a voltage measuring device electrically connected to the second piezoelectric element of the pair of the piezoelectric elements, and a crack detector electrically connected to the power source and the voltage measuring device.

The power source is to apply voltage to the first piezoelectric element to cause deformation in the first piezoelectric element, the voltage measuring device is to measure voltage generated from the second piezoelectric element that is forcibly deformed according to the deformation of the first piezoelectric element, the crack detector is to obtain from the power source a value of the applied voltage to the first piezoelectric element and from the voltage measuring device a value of the measured voltage, to find a transfer function of the pair of the piezoelectric elements based on the values of the applied voltage and the measured voltage, and to detect presence or absence of a crack in one or both of the pair of the piezoelectric elements based on an objective value obtained from the found transfer function.

Hereinafter, the embodiment of the present invention will be explained in detail with reference to drawings.

FIG. 1 is a general view schematically illustrating a crack detecting apparatus for piezoelectric elements according to the embodiment of the present invention.

The crack detecting apparatus 1 according to the embodiment is provided with an AC power source 3, a voltage measuring device 5, and a crack detector 7 and detects presence or absence of a crack in one or both of a pair of piezoelectric elements 9a and 9b.

The pair of the piezoelectric elements 9a and 9b are united with each other and are deformable integrally as a piezoelectric actuator or the like. According to the embodiment, the pair of the piezoelectric elements 9a and 9b compose a piezoelectric actuator used in a head suspension incorporated in a hard disk drive and are attached to an actuator base 11. In FIG. 1, the piezoelectric elements 9a and 9b and the actuator base 11 are illustrated as a plan view and the other components and electrical connections are schematically or conceptually illustrated.

The actuator base 11 is a thin plate composing a part of the head suspension and has openings 13a and 13b. The openings 13a and 13b are located in the middle of the actuator base 11 in a longitudinal direction of the head suspension that is a vertical direction of FIG. 1 and are extended from both side edges to the middle of the actuator base 11 in a lateral direction of the head suspension that is a right and left direction of FIG. 1. With this, the actuator base 11 is provided with a stationary member 15, a movable member 17 and a connecting part 19.

The stationary member 15 and the movable member 17 are formed into a rectangular planar shape elongated in the lateral direction. The stationary member 15 and the movable member 17 are not limited to the rectangular planar shape and may be formed into any other shapes in so far as the movable member 17 is allowed to be displaced relative to the stationary member 15 as a piezoelectric actuator or the like. The stationary member 15 and the movable member 17 are opposite to each other across the openings 13a and 13b in the longitudinal direction and are connected to each other at the widthwise centers.

The connecting part 19 is formed into a rectangular planar shape elongated in the longitudinal direction. The connecting part 19 connects the movable member 17 and the stationary member 15 to allow the movable member 17 to displace relative to the stationary member 15. According to the embodiment, the movable member 17 is tiltable about the connecting part 19. The connecting part 19 is not limited to the rectangular planar shape and may be formed into any other shapes in so far as the connecting part 19 allows the movable member 17 to displace relative the stationary member 15.

On the actuator base 11, the pair of the piezoelectric elements 9a and 9b are arranged on both sides of the connecting portion 19 in the lateral direction so that the piezoelectric elements 9a and 9b cross the respective openings 13a and 13b in the longitudinal direction. The piezoelectric elements 9a and 9b are thin plates formed into a rectangular planar shape elongated in the longitudinal direction. The longitudinal ends of each one of the piezoelectric elements 9a and 9b are fixed to the stationary member 15 and the movable member 17 by adhesives (not illustrated), respectively. The piezoelectric elements 9a and 9b are parallel with each other and have opposite polarities. With this, the piezoelectric elements 9a and 9b are longitudinally deformable in opposite directions according to voltage applied thereto so that one of the piezoelectric elements 9a and 9b is contracted and the other thereof is elongated in the longitudinal direction. In this embodiment, the elongation and contraction direction of the piezoelectric elements 9a and 9b is the longitudinal direction and the orthogonal direction relative to the elongation and contraction direction is the lateral direction.

The AC power source 3 is electrically connected to one of the piezoelectric elements 9a and 9b in particular the first piezoelectric element 9a to apply voltage to the first piezoelectric element 9a. The AC power source 3 is configured to enable a frequency value and a voltage (AC voltage) value to be set within given ranges. The AC power source 3, therefore, outputs and applies voltage having a set frequency value and a set voltage value to the first piezoelectric element 9a. According to this application of the voltage, the first piezoelectric element 9a is elongated or contracted (deformed). As the power source, a DC power source may be employed instead of the AC power source 3 in principle.

If the first piezoelectric element 9a is deformed as mentioned above, the movable member 17 of the actuator base 11 is displaced about the connecting part 19 relative to the stationary member 15 according to the deformation of the first piezoelectric element 9a. With this displacement of the movable member 17, the other of the piezoelectric elements 9a and 9b in particular the second piezoelectric element 9b is forcibly elongated or contracted (deformed) in the opposite direction relative to the first piezoelectric element 9a. For example, if the first piezoelectric element 9a is elongated, the second piezoelectric element 9b is oppositely contracted. As a result, the second piezoelectric element 9b generates voltage.

The voltage measuring device 5 is electrically connected to the second piezoelectric element 9b so that the voltage generated at the second piezoelectric element 9b is input to the voltage measuring device 5. The voltage measuring device 5, therefore, measures the input voltage generated from the second piezoelectric element 9b.

The crack detector 7 detects presence or absence of a crack in one or both of the pair of the piezoelectric elements 9a and 9b based on the values of the applied voltage to the first piezoelectric element 9a from the AC power source 3 and the measured voltage generated from the second piezoelectric element 9b and measured by the voltage measuring device 5.

The crack detector 7 includes a computer having a CPU (central processing unit), a RAM (random access memory), a ROM (read only memory) and the like and to executing programs to fulfill functions. The crack detector 7 may be a single unit integrated with one or both of the AC power source 3 and the voltage measuring device 5 though it is a discrete unite separated from the AC power source 3 and the voltage measuring device 5 in FIG. 1.

The crack detector 7 is electrically connected to the AC power source 3 and the voltage measuring device 5. The crack detector 7 has a first function to obtain from the AC power source 3 the value of the applied voltage to the first piezoelectric element 9a and from the voltage measuring device 5 the value of the measured voltage.

For the obtaining of the values of the applied voltage and the measured voltage, the AC power source 3 outputs to the crack detector 7 the value of the output voltage in response to the output of the voltage to be the applied voltage as a trigger and the voltage measuring device 5 outputs to the crack detector 7 the value of the input voltage in response to the input or the measurement of the voltage as a trigger. The way to obtain the values of the applied voltage and the measured voltage is not limited to the above in so far as the crack detector 7 obtains the values. For example, the crack detector 7 may request the AC power source 3 and the voltage measuring device 5 to output the values of the applied voltage and the measured voltage.

Figure 2:
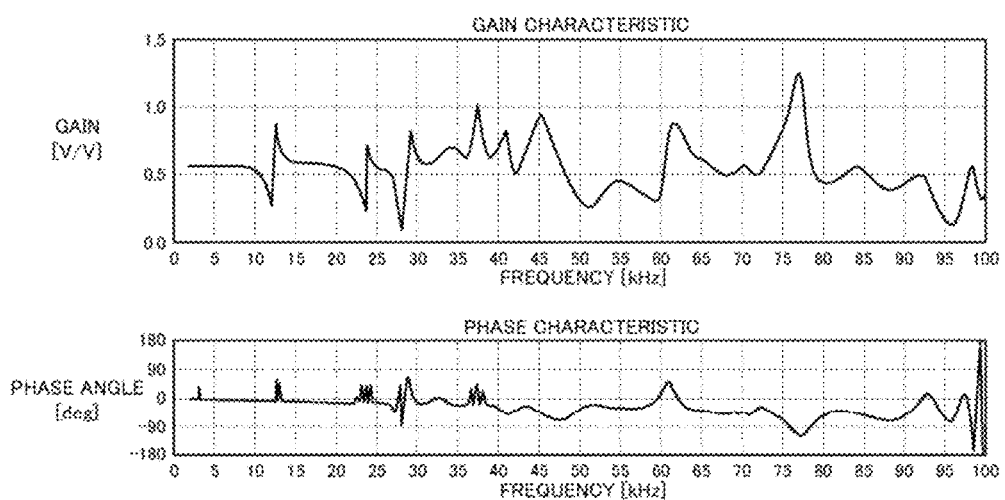
FIG. 2 is a graph illustrating examples of a gain characteristic and a phase characteristic of a frequency transfer function according to the embodiment.

Further, the crack detector 7 has a second function to find a transfer function of the pair of the piezoelectric elements 9a and 9b based on the obtained values of the applied voltage and the measured voltage. The transfer function is expressed by G(s)=Y(s)/X(s) in which Y(s) means a function of an output and X(s) means a function of an input. According to the embodiment, the transfer function of this embodiment is a frequency transfer function. FIG. 2 is a graph illustrating examples of a gain characteristic and a phase characteristic of a frequency transfer function. In principle, the transfer function is not limited to the frequency transfer function.

Further, the crack detector 7 has a third function to detect presence or absence of a crack in one or both of the pair of the piezoelectric elements 9a and 9b based on an objective value obtained from the found transfer function.

According to the embodiment, the objective value is a peak value, an area value or a frequency value obtained from waveforms of the gain characteristic and the phase characteristic of the frequency transfer function. The detection of a crack based on the objective value is realized by comparing the objective value with a reference value or evaluating the objective value using a discriminant. The objective value, the reference value and the discriminant will be explained later in detail.

The crack detecting method enables a very fine micro crack in the pair of the piezoelectric element 9a and 9b to be detected. Namely, the crack detecting method of this embodiment surely detects a crack in piezoelectric elements regardless of size of the crack.

Figure 3A:
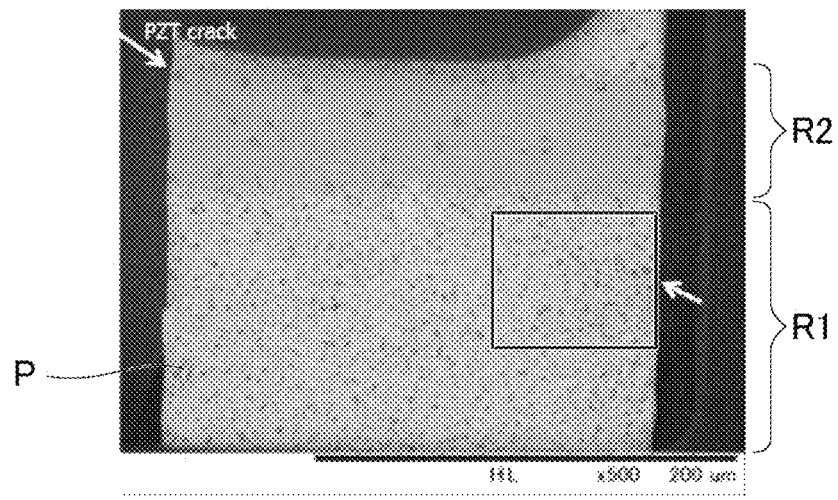
FIG. 3A is an enlarged photograph of a piezoelectric element with a micro crack.
Figure 3B:
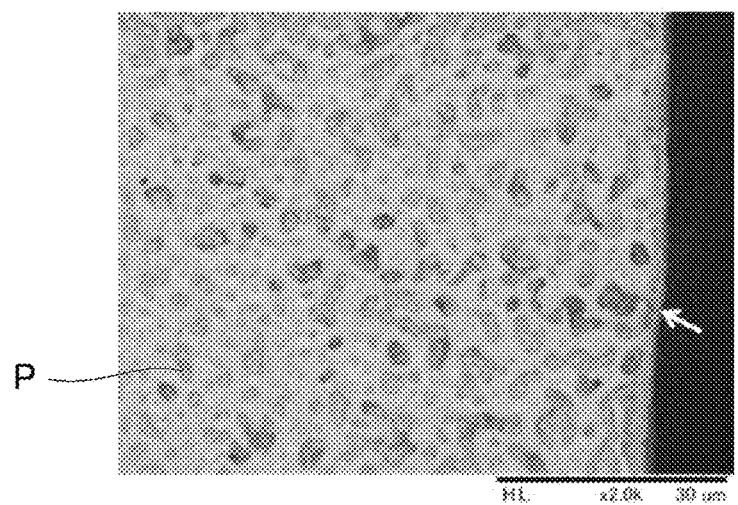
FIG. 3B is an enlarged photograph of part of FIG. 3A.
Figure 5A:
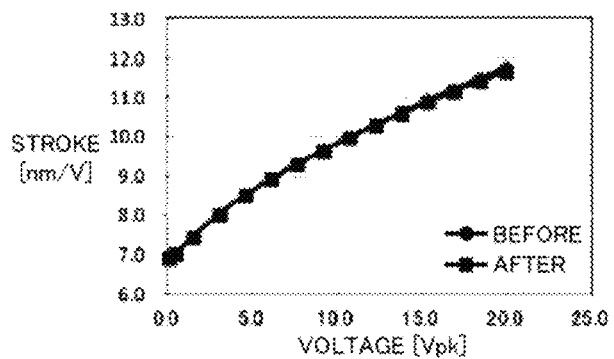
FIGS. 5A to 5D are graph measurement results of strokes of piezoelectric elements before and after crack generation.
Figure 5B:
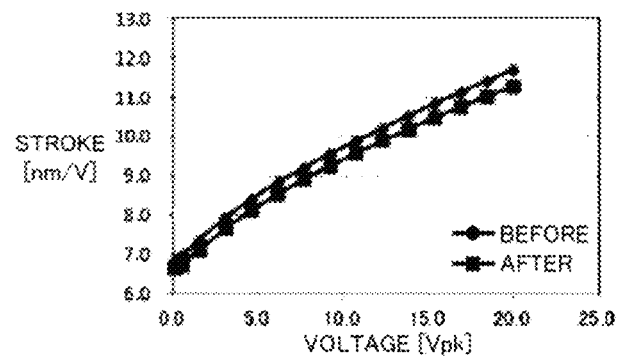
Figure 5C:
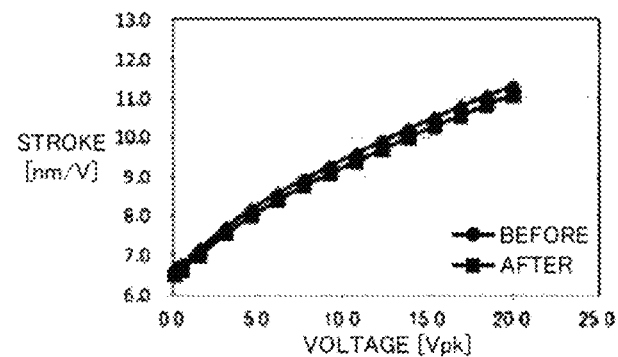
Figure 5D:
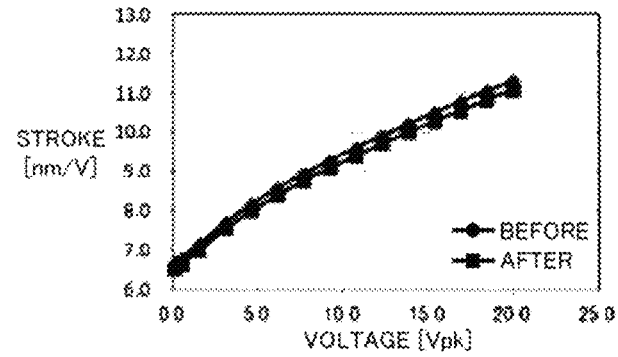

FIG. 3A is an enlarged photograph of a piezoelectric element with a micro crack and FIG. 3B is an enlarged photograph of part of FIG. 3A.

As a micro crack, there is a very fine micro crack that can never be found from appearance in a region R1 with a gold plate P and that is hard to be found from appearance in a region R2 without a gold plate P. Such a very fine micro crack (hereinafter, referred to simply as fine micro crack) does not affect on electric characteristics and therefore is overlooked in crack detection based on the electric characteristics.

FIG. 4 is a table of measurement results of electric characteristics of cracked and crackless piezoelectric elements. In FIG. 4, indicated are values of capacitances and dielectric loss tangents that are measured from five samples of piezoelectric elements as the electric characteristics before and after crack generation in a case where a fine micro crack is artificially caused in each sample. The columns "BEFORE" in FIG. 4 indicate the values before the crack generation and the columns "AFTER" indicate the values after the crack generation.

As illustrated in FIG. 4, there are no great changes in capacitance and dielectric loss tangent before and after the crack generation.

FIG. 5 is a graph measurement results of strokes of cracked and crackless piezoelectric elements. In FIG. 5, indicated are curves based on plotted strokes that are measured from a sample of a piezoelectric element before and after crack generation in a case where a fine micro crack is artificially caused in each sample like FIG. 4.

As illustrated in FIG. 5, there are no great changes in the strokes before and after the crack generation.

Figure 6:
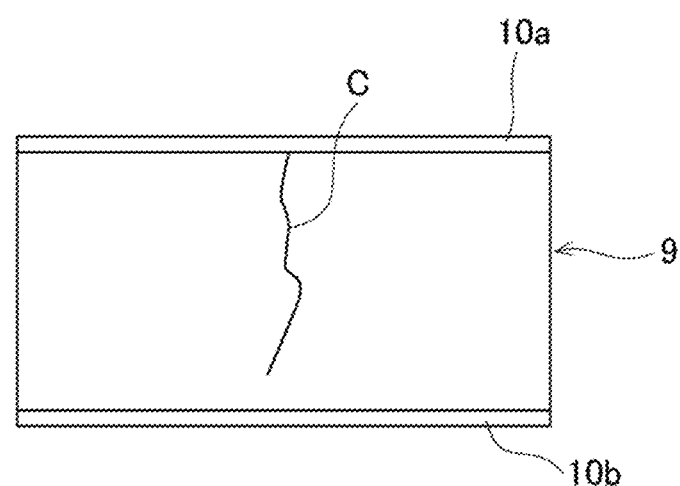
FIG. 6 is a sectional view schematically illustrating a piezoelectric element with a micro crack and undivided electrodes.

In this way, a fine micro crack does not cause great changes in capacitance, dielectric loss tangent and stroke whereas a relative large normal micro crack causes great changes in capacitance, dielectric loss tangent and stroke. This is based on the fact that electrodes of a piezoelectric element with a fine micro crack are not completely divided. FIG. 6 is a sectional view schematically illustrating an example of a piezoelectric element 9 with a fine micro crack C and undivided electrodes 10a and 10b. The electrodes 10a and 10b may be gold plating, platinum plating or the like and in this embodiment are platinum plating.

Even such a fine micro crack deteriorates long-term reliability of a piezoelectric actuator and needs to be surely detected.

Then, the embodiment finds the frequency transfer function of the pair of the piezoelectric elements 9a and 9b and compares one or more objective values obtained from the gain characteristic and/or the phase characteristic of the found transfer function with respective reference values or evaluates one or more objective values using the discriminant, thereby to enable a fine micro crack to be detected.

In particular, the present embodiment applies voltage to only the first piezoelectric element 9a and finds the frequency transfer function based on values of the applied voltage to the first piezoelectric element 9a and the generated voltage from the second piezoelectric element 9b. This enables a fine micro crack in the pair of the piezoelectric elements 9a and 9b to be detected using the objective values obtained from the transfer function in particular the frequency transfer function.

Figure 7:
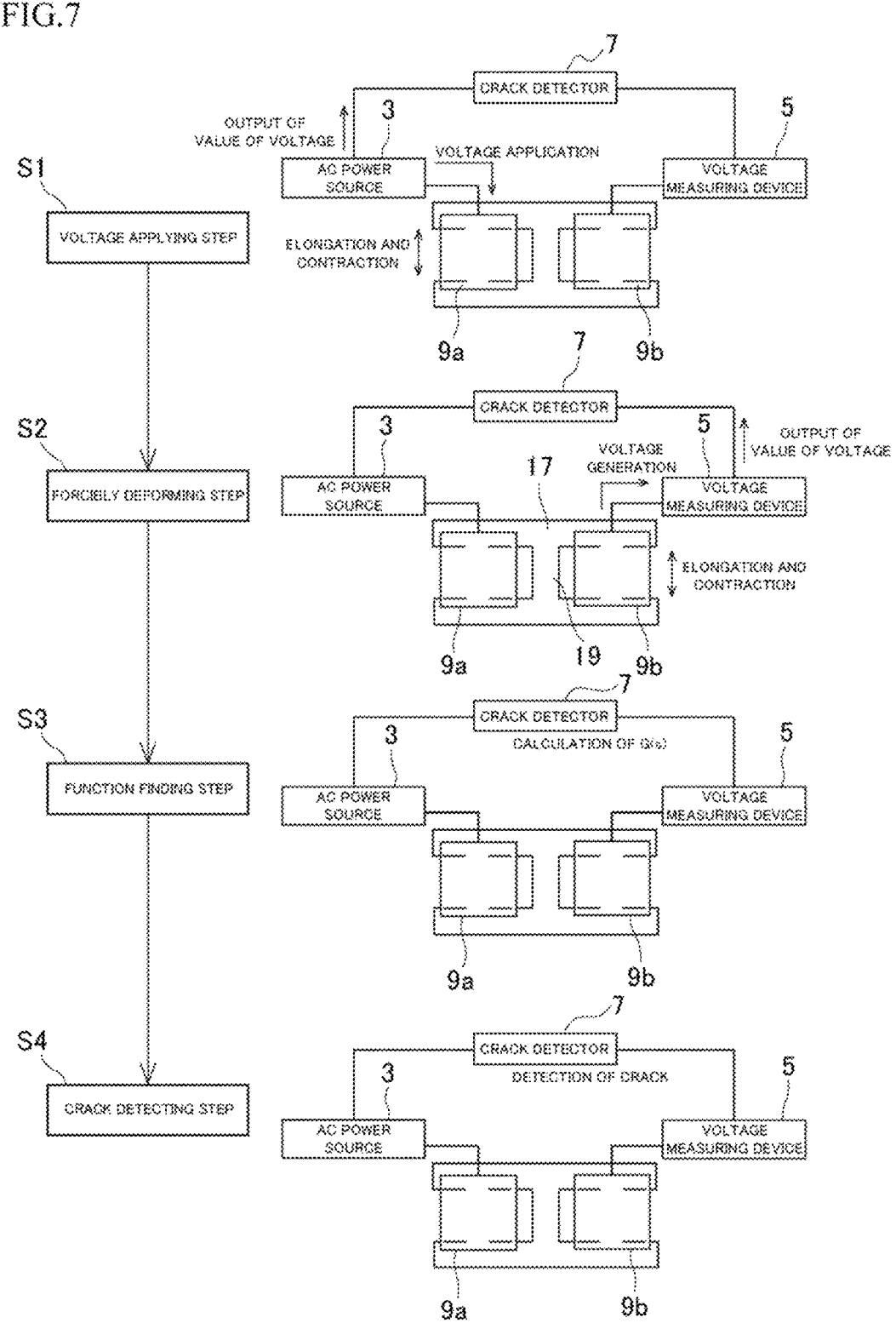
FIG. 7 is a flow chart of a crack detecting method according to the embodiment.

FIG. 7 is a flow chart of the crack detecting method.

The crack detecting method according to the embodiment sequentially performs a voltage applying step S1, a forcibly deforming step S2, a function finding step S3 and a crack detecting step S4.

In the voltage applying step S1, the AC power source 3 applies voltage with a set voltage value and a set frequency value to the first piezoelectric element 9a of the pair of the piezoelectric elements 9a and 9b that are measuring objects. The value of the applied voltage is output from the AC power source 3 to the crack detector 7. The voltage application may be controlled by the crack detector 7 as a controller. According to the voltage application, the piezoelectric element 9a is deformed.

In the forcibly deforming step S2, the second piezoelectric element 9b of the pair of the piezoelectric elements 9a and 9b is forcibly deformed according to the deformation of the first piezoelectric element 9a. Namely, the deformation of the first piezoelectric element 9a causes the movable member 17 of the actuator base 11 to be displaced about the connecting part 19, thereby to forcibly deform the second piezoelectric element 9b to be elongated or contracted in the opposite direction relative to the deformation of the first piezoelectric element 9a.

At this time, the second piezoelectric element 9b generates voltage according to the forced elongation or contraction of the second piezoelectric element 9b. The generated voltage is measured at the voltage measuring device 5 and the measuring device 5 outputs the measured value of the generated voltage to the crack detector 7.

In the function finding step S3, the crack detector 7 finds the frequency transfer function G(s) using the value of the applied voltage that is input from the AC power source 3 and the value of the measured voltage (generated voltage) that is input from the measuring device 5. The method of finding the transfer function is commonly-known and is omitted here.

In the crack detecting step S4, the crack detector 7 obtains one or more objective values in particular peak values, area values, or frequency values in the gain characteristic and the phase characteristic or any combination of these values from the frequency transfer function found in the function finding step S3. Then, the crack detector 7 compares the objective values with respective reference values or evaluates the objective values using the discriminant, thereby to detect a crack in one or both of the pair of the piezoelectric elements 9a and 9b.

Hereinafter, comparison between objective values and reference values will be explained with reference to FIGS. 8A to 14 as well as test results. First, the test results for finding the reference values will be explained.

Figure 8A:
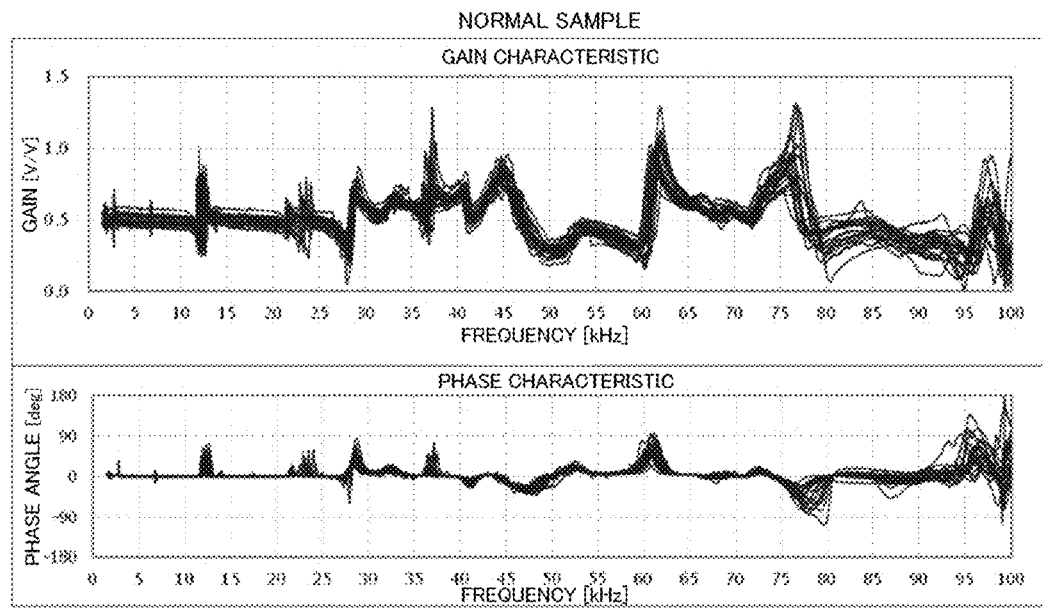
FIGS. 8A and 8B are graphs illustrating gain characteristics and phase characteristics of frequency transfer functions obtained from normal and error samples.
Figure 8B:
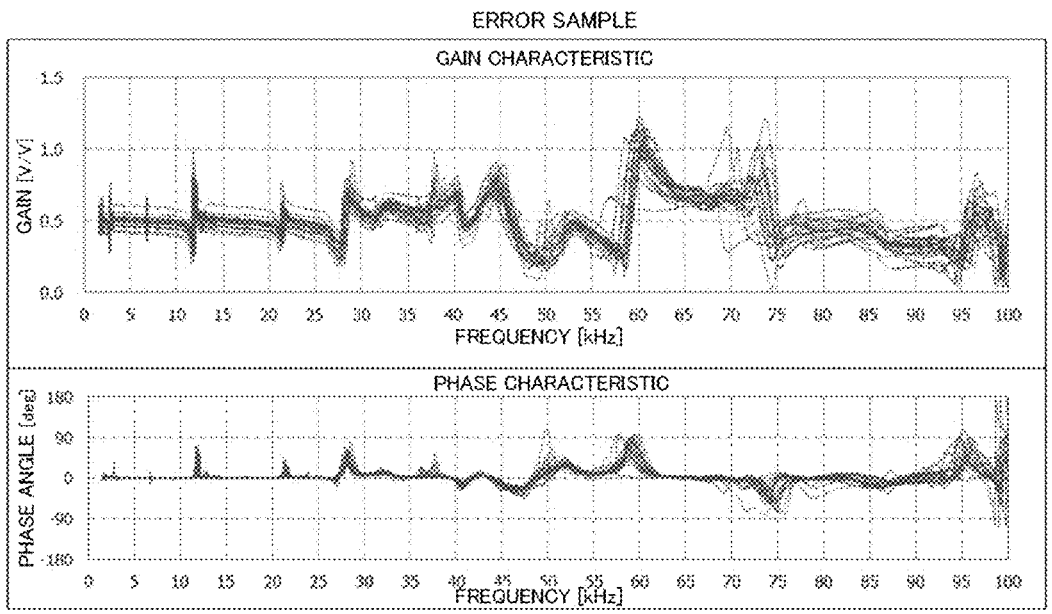
Figure 9:
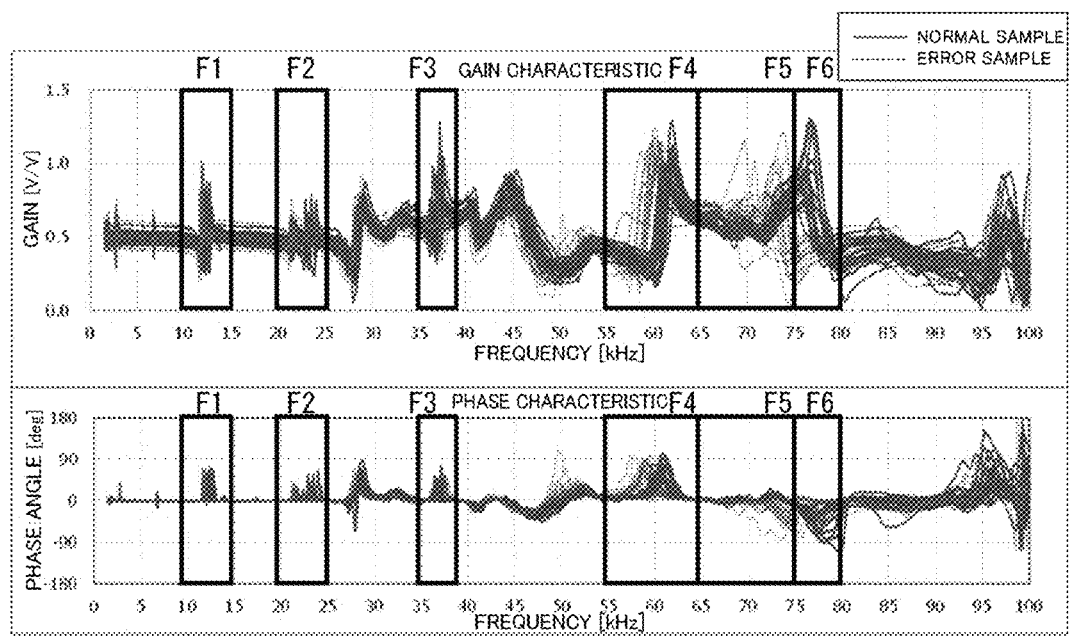
FIG. 9 is a graph illustrating superimposed gain characteristics of FIGS. 8A and 8B and superimposed phase characteristics of FIGS. 8A and 8B.

FIGS. 8A and 8B are graphs illustrating gain characteristics and phase characteristics of frequency transfer functions obtained from normal samples without micro cracks and error samples with micro cracks in which FIG. 8A is for the normal samples without the micro cracks and FIG. 8B the error samples with the micro cracks. FIG. 9 is a graph illustrating superimposed gain characteristics of FIGS. 8A and 8B and superimposed phase characteristics of FIGS. 8A and 8B.

FIG. 8A represents the waveforms of the frequency transfer functions (hereinafter referred to as normal transfer functions) found from plural normal samples in particular twenty normal samples in which both piezoelectric elements in each normal sample are not cracked. FIG. 8B represents the waveforms of the frequency transfer functions (hereinafter referred to as error transfer functions) found from plural error samples in particular twenty error samples in which one or both piezoelectric elements in each error sample are cracked. As the cracks of the error samples, fine micro cracks are artificially caused in the piezoelectric elements of the error samples in the same way as the above.

The error transfer functions and the normal transfer functions are found using the crack detecting apparatus 1 by values of voltage applied to a first piezoelectric element 9a and voltage generated from a second piezoelectric element in each sample. In some error samples, only a first piezoelectric element 9a has a micro crack. In some other error samples, only a second piezoelectric element 9b has a micro crack. In some still other error samples, both first and second piezoelectric elements 9a and 9b have micro cracks, respectively. Among these error samples, there are no great changes in the waveforms of the transfer functions. Thus, the crack detecting method has only to apply voltage to the first piezoelectric element 9a as mentioned above and this enables a micro crack to be rapidly detected.

Comparing the results of FIGS. 8A and 8B by superimposing the same as illustrated in FIG. 9, there are deviations in frequencies at which corresponding peaks appears in the gain characteristics and the phase characteristics between the error transfer functions and the normal transfer functions. The deviations are focused to compare values obtained from the corresponding peaks in the gain characteristics and the phase characteristics involving the deviations.

In particular, frequency ranges F1 to F6 are defined on the error and normal transfer functions for a plurality groups of the corresponding peaks involving the deviations so that each frequency range includes a single group (focused group) of the corresponding peaks and does not include adjacent groups of the corresponding peaks around the focused group of the corresponding peaks. Then, the peak values, the area values or the frequency values of the peaks in each frequency range are extracted from the error and normal transfer functions as values of selected parameters and are compared between the error transfer functions and the normal transfer functions. The peak value is a value of a peak top of a peak, the area value is a value of a peak area of a peak and the frequency value is a value of a frequency at which a peak top appears.

Figure 10A:
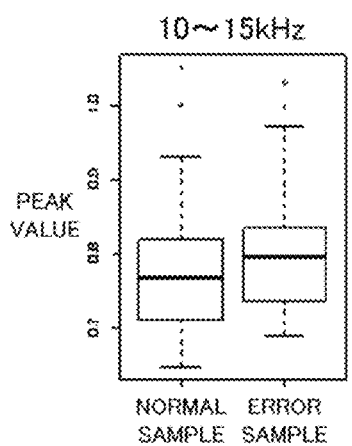
FIGS. 10A to 10F are box-and-whisker plots illustrating distributions of peak values in frequency ranges set on the gain characteristics of the transfer functions of the error samples and the normal samples of FIG. 9.
Figure 10B:
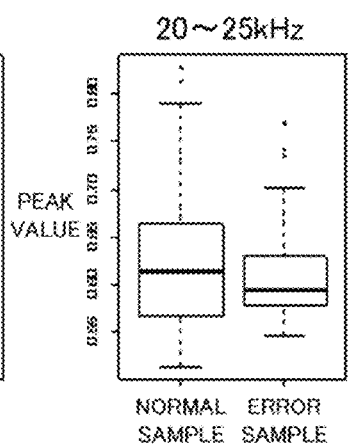
Figure 10C:
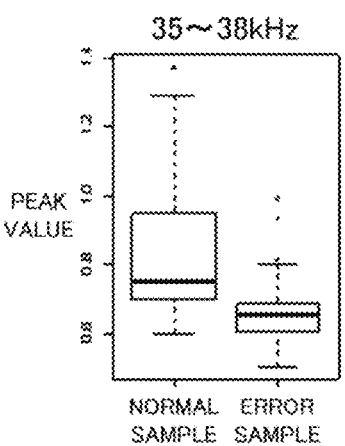
Figure 10D:
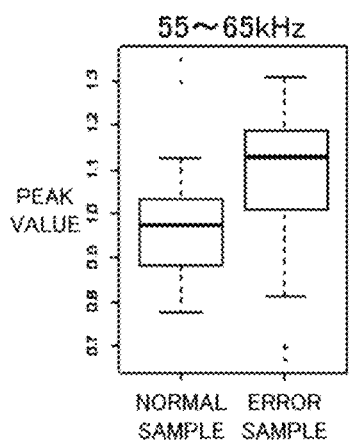
Figure 10E:
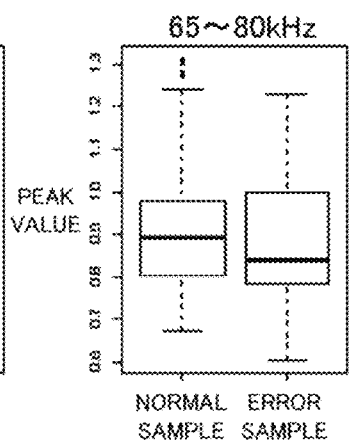
Figure 10F:
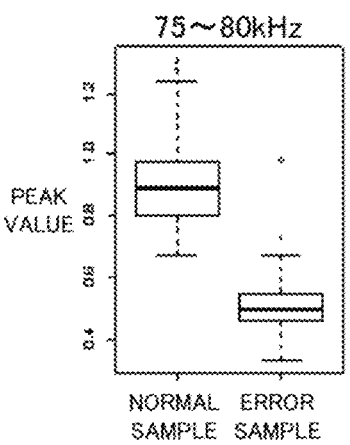
Figure 11A:
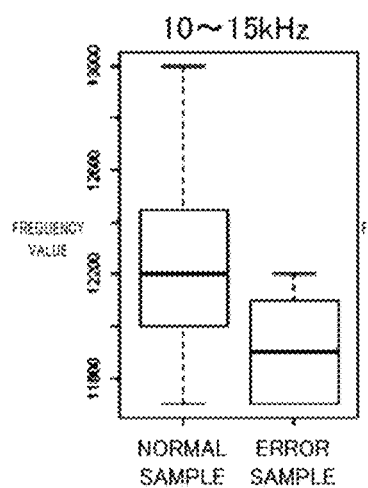
FIGS. 11A to 11F are box-and-whisker plots illustrating distributions of frequency values in respective frequency ranges set on the gain characteristics of the transfer functions of the error samples and the normal samples of FIG. 9.
Figure 11B:
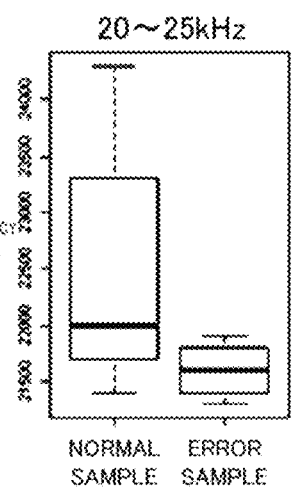
Figure 11C:
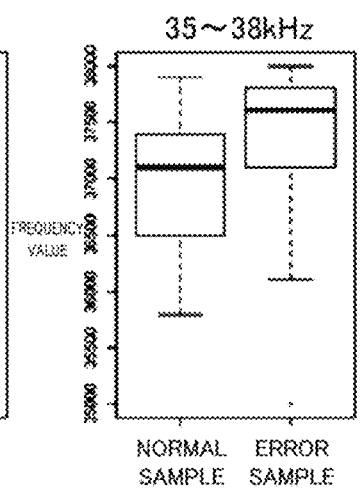
Figure 11D:
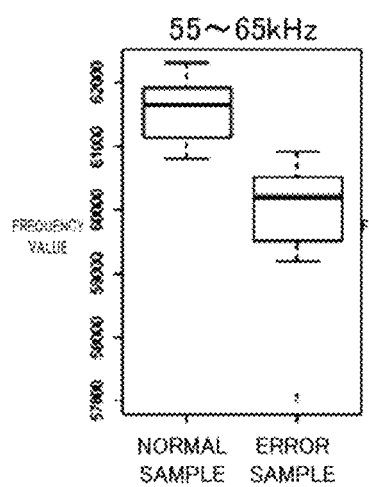
Figure 11E:
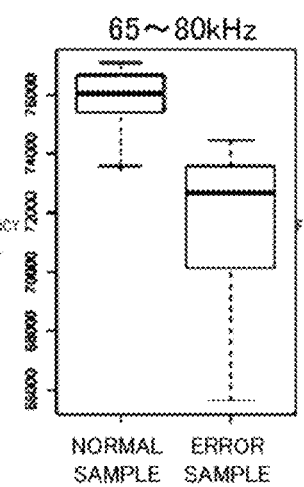
Figure 11F:
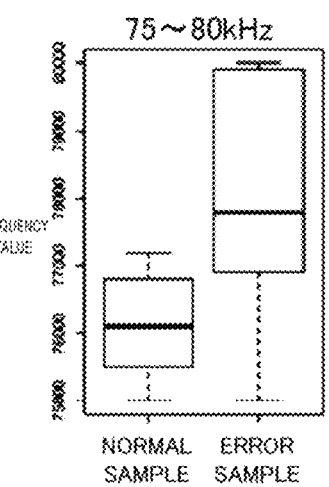
Figure 14A:
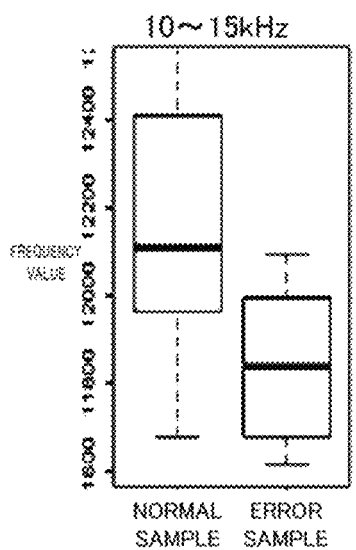
FIGS. 14A to 14F are box-and-whisker plots illustrating distributions of frequency values in respective frequency ranges set on the phase characteristics of the transfer functions of the error samples and the normal samples of FIG. 9.
Figure 14B:
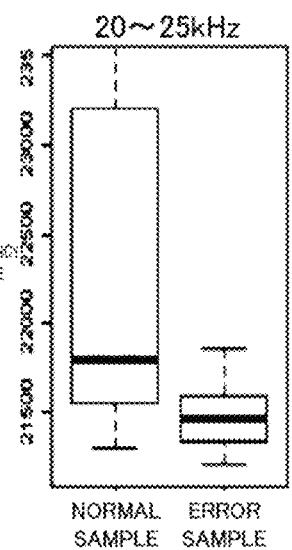
Figure 14C:
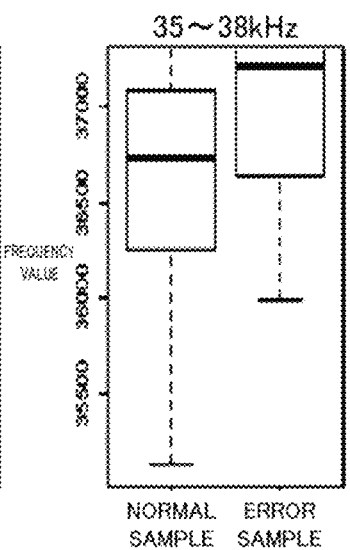
Figure 14D:
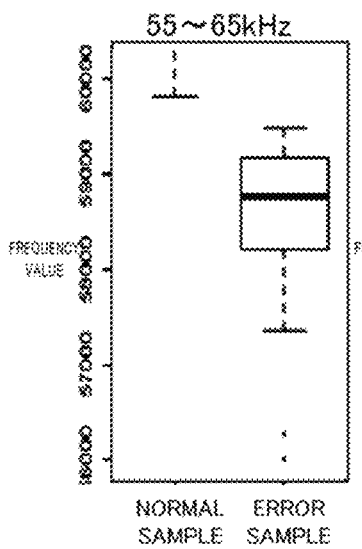
Figure 14E:
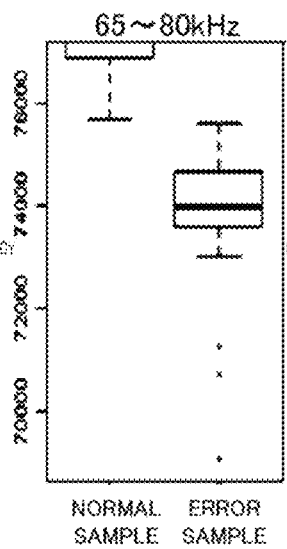
Figure 14F:
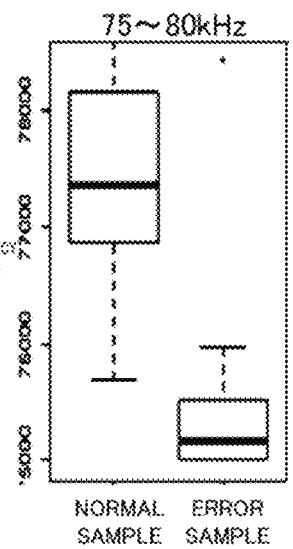

FIGS. 10A to 10F are box-and-whisker plots illustrating distributions of the peak values in different frequency ranges of the gain characteristics of the error transfer functions (error samples) and the normal transfer functions (normal samples) of FIG. 9. FIG. 10A represents the distributions in the frequency range F1 of 10 kHz to 15 kHz, FIG. 10B the frequency range F2 of 20 kHz to 25 kHz, FIG. 10C the frequency range F3 of 35 kHz to 38 kHz, FIG. 10D the frequency range F4 of 55 kHz to 65 kHz, FIG. 10E the frequency range F5 of 65 kHz to 80 kHz and FIG. 10F the frequency range F6 of 75 kHz to 80 kHz.

In each box-and-whisker plot of FIGS. 10A to 10F, the box represents first and third quartiles, the thick line in the box represents the average, the upper and the lower lateral lines represents the maximum and the minimum values, respectively, and the dots outside the maximum and the minimum values are outliers. The same holds for the box-and-whisker plots in the other drawings.

As illustrated in FIGS. 10A to 10F, the error samples and the normal samples partly overlap each other in a value range spanning from the maximum value to the minimum value of the peak values of the gain characteristics in all the frequency ranges F1 to F6. Thus, the peak values in the gain characteristics do not enable the group of the error samples and the group of the normal samples to be accurately divided from each other. Namely, the peak values in the gain characteristics are not sufficient for precisely discriminating between presence and absence of a fine micro crack in the piezoelectric elements.

FIGS. 11A to 11F are box-and-whisker plots illustrating distributions of frequency values in the respective frequency ranges F1 to F6 of the gain characteristics of the error transfer functions and the normal transfer functions of FIG. 9.

As illustrated in FIGS. 11A to 11F, the error samples and the normal samples partly overlap each other in a value range spanning from the maximum value to the minimum value of the frequency values of the gain characteristics in all the frequency ranges F1 to F6. Namely, the frequency values in the gain characteristics are not sufficient for precisely discriminating between presence and absence of a fine micro crack in the piezoelectric elements.

FIGS. 12A to 12C are box-and-whisker plots illustrating distributions of area values in different frequency ranges of the gain characteristics of the error transfer functions and the normal transfer functions of FIG. 9. FIG. 12A represents the distributions in the frequency range F7 of 70 kHz to 80 kHz, FIG. 12B the frequency range F6 of 75 kHz to 80 kHz, and FIG. 12C the frequency range F8 of 76 kHz to 80 kHz. FIGS. 12A to 12C only represent the frequency ranges F6 to F8 that seem most likely to discriminate between the error samples and the normal samples. The frequency ranges F1 to F5 are not illustrated. The frequency ranges F7 and F8 are the modified frequency ranges F5 and F6.

As illustrated in FIGS. 12A to 12C, the error samples and the normal samples partly overlap each other in a value range spanning from the maximum value to the minimum value of the area values of the gain characteristics even in the frequency ranges not only F1 to F5 but also F6 to F8. Namely, the area values in the gain characteristics are not sufficient for precisely discriminating between presence and absence of a fine micro crack in the piezoelectric elements.

Each area value in FIGS. 12A to 12C is an area value vertically between an abscissa and a part of the waveform spanning laterally between ends of the corresponding frequency range as illustrated in FIG. 13. FIG. 13 is an example for finding an area value in the frequency range F6 of 75 kHz to 80 kHz.

In the phase characteristics, the peak values and the area values are not sufficient for precisely discriminating between presence and absence of a fine micro crack in the piezoelectric elements. In contrast, the frequency values in the phase characteristics enable in the particular frequency ranges to discriminate between presence and absence of a fine micro crack in a piezoelectric element.

FIGS. 14A to 14F are box-and-whisker plots illustrating distributions of frequency values in the respective frequency ranges F1 to F6 of the phase characteristics of the error transfer functions and the normal transfer functions of FIG. 9. In FIGS. 14A to 14F, values are widely dispersed and therefore only essential parts of the box-and-whisker plots are illustrated.

As illustrated in FIGS. 14A to 14F, the error samples and the normal samples do not overlap each other in a value range spanning from the maximum value to the minimum value of the frequency values of the phase characteristics in the frequency range F4 of 55 kHz to 65 kHz and the frequency range F5 of 65 kHz to 80 kHz. Accordingly, the frequency values of the phase characteristics result in surely dividing the group of the error samples and the group of the normal samples from each other and enable to discriminate between presence and absence of a fine micro crack in a piezoelectric element.

In the case of FIGS. 14A to 14F, the frequency values of the phase characteristics of the error transfer functions are less than those of the normal transfer functions in the frequency range F4 of 55 kHz to 65 kHz and the frequency range F5 of 65 kHz to 80 kHz.

Thus, the maximum frequency value in the phase characteristics of the error transfer functions or the minimum frequency value in the phase characteristics of the normal transfer functions is used as a reference value in one or both of the frequency ranges F4 and F5, thereby to detect presence or absence of a fine micro crack.

For more details, the crack detecting method compares the objective value in particular the frequency value in the phase characteristic obtained from the frequency transfer function of the pair of the piezoelectric elements 9a and 9b that are measuring objects with the reference value and determines that the objective value is less or greater than the reference value in one or both frequency ranges F4 and F5, to detect presence or absence of a crack in one or both of the pair of the piezoelectric elements.

The reference value may be selected from a value obtained from a transfer function of at least one error sample or at least one normal sample of a pair of piezoelectric elements instead of the maximum value or the minimum value selected from the values obtained from the transfer functions of the plural error samples and the plural normal samples.

Both the maximum value in the phase characteristics of the error transfer functions and the minimum value in the phase characteristics of the normal transfer functions may be used as reference values.

Frequency ranges and parameters that enable a fine micro crack to be detected should be used suitable for a specification of a piezoelectric actuator and therefore should be set through tests or the like.

Hereinafter, evaluation based on the objective value using a discriminant will be explained with reference to FIGS. 15 to 20B as well as test results.

In order to find a discriminant, discriminant analysis is performed using values obtained from the error transfer functions and the normal transfer functions as error values and normal values, respectively. The method of the discriminant analysis is commonly-known and is omitted here.

According to the embodiment, two parameters are selected from plural parameters in particular respective two group of parameters and discriminant analysis is performed to the error samples and the normal samples using the error values and the normal values of the selected two parameters. Such discriminant analysis is performed in a round robin to the plural parameters, i.e., the two groups of the parameters. For the discriminant analyses, this embodiment chooses 38 error samples and 40 normal samples.

Figure 15:
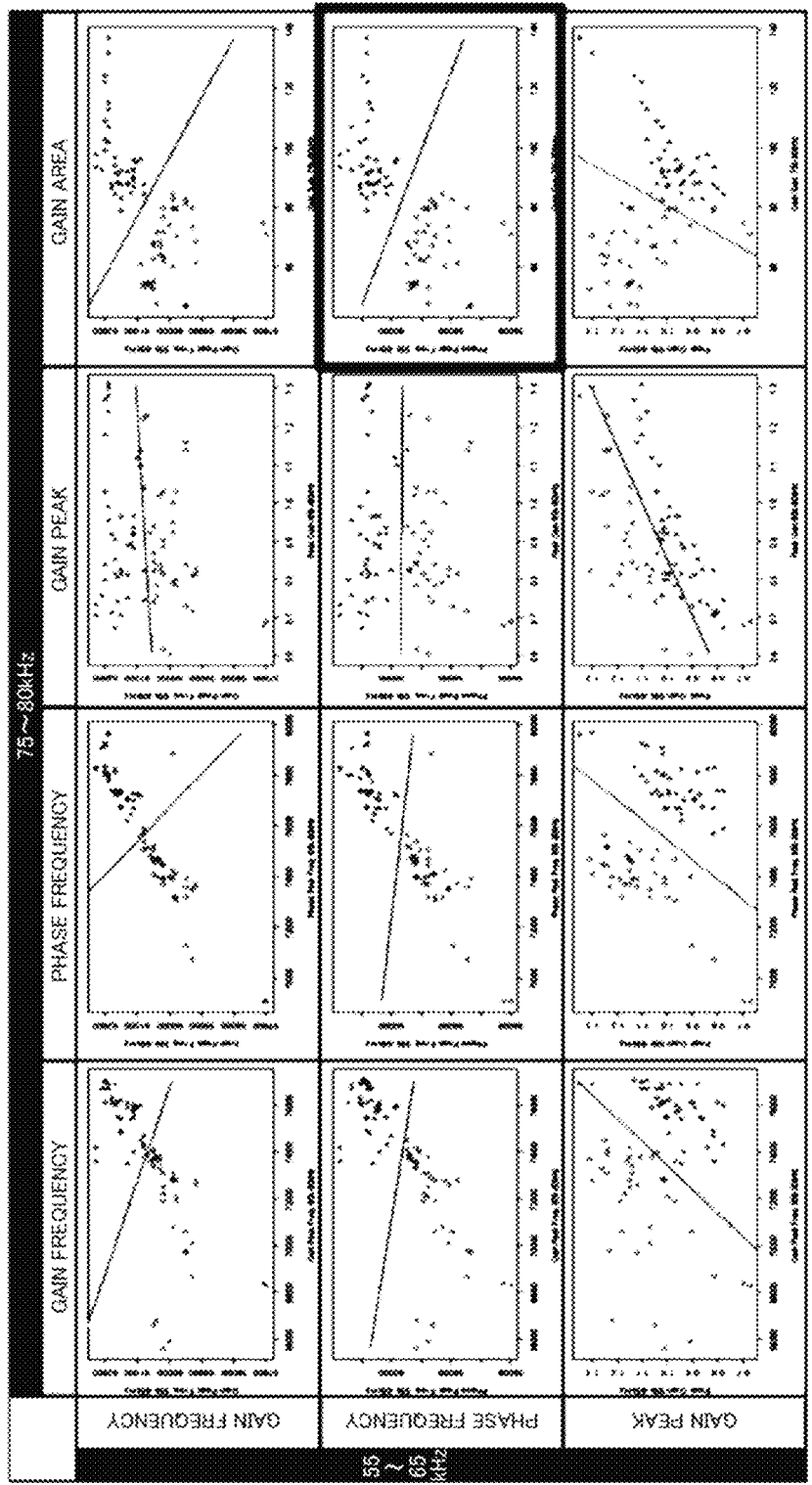
FIG. 15 is a table illustrating results of discriminant analyses each conducted using two parameters selected from respective two groups of parameters that are obtained from the transfer functions of the error samples and the normal samples of FIG. 9.

FIG. 15 is a table illustrating results of discriminant analyses each conducted using two parameters selected from the respective two groups of the parameters obtained from the error transfer functions and the normal transfer functions of FIG. 9. FIG. 16 is a graph illustrating the result of the discriminant analysis that completely discriminates between the error samples and the normal samples in FIG. 15.

FIG. 15 selectively represents as parameters the peak value in the gain characteristic (gain peak), the frequency value in the gain characteristic (gain frequency), and the frequency value in the phase characteristic (phase frequency) in the frequency range F4 of 55 kHz to 65 kHz, and the peak value, the frequency value and the area value (gain area) in the gain characteristic and the frequency value in the phase characteristic in the frequency range F6 of 75 kHz to 80 kHz.

In graphs of the respective cells of the grid of FIG. 15, an ordinate indicates a leftmost parameter in a row to which a cell belongs and an abscissa indicates an uppermost parameter in a column to which a cell belongs.

FIG. 15 approximately illustrates which combination of two parameters can discriminate between the error samples and the normal samples regardless of numerical values and characters that are unclear in the graphs of the respective cells.

Further, FIG. 15 does not illustrate the area value in the gain characteristic, the peak value and the area value in the phase characteristic even in the frequency range 55 kHz to 65 kHz, and the peak value and the area value in the phase characteristic even in the frequency range 75 kHz to 80 kHz. These parameters do not discriminate between the error samples and the normal samples at all. Similarly, the discriminant results in the other frequency ranges are not illustrated because they do not discriminate between the error samples and the normal samples at all.

It is understood from FIGS. 15 and 16 that the discrimination analysis is conducted using as two parameters the frequency value in the phase characteristic in the frequency range F4 of 55 kHz to 65 kHz and the area value in the gain characteristic in the frequency range F6 of 75 kHz to 80 kHz, thereby to completely and precisely discriminate between the error samples and the normal samples.

FIGS. 17 and 18 illustrate the result of the discriminant analysis (discriminant result) of FIG. 16 in which FIG. 17 is a graph classifying the error and normal samples at values obtained by the discriminant in FIG. 16 and FIG. 18 is a table illustrating discriminant results of the error and normal samples determined as error and normal products.

As illustrated in FIG. 17, the discriminant analysis of FIG. 16 determines a sample having a value of Y that is less than 0 (Y<0) in the discriminant or the discriminant function Y=a0+a1*x1+a2*x2 as a normal product and a sample having a value of Y that exceeds 0 (Y>0) as an error product. As illustrated in FIG. 18, the error samples are correctly determined as the error products and the normal samples the normal products.

In the discriminant function, a0 is a constant term, a1 and a2 are coefficients, and x1 and x2 are the frequency value in the phase characteristic in the frequency range 55 kHz to 65 kHz and the area value in the gain characteristic in the frequency range 75 kHz to 80 kHz that are the parameters in this embodiment. The constant term a0 and the coefficients a1 and a2 can be obtained in the same way as the commonly-known method.

Thus, the discriminant function of the discriminant analysis of FIG. 16 is used as the discriminant to detect presence or absence of a fine micro crack. In particular, the frequency value in the phase characteristic in the frequency range 55 kHz to 65 kHz and the area value in the gain characteristic in the frequency range 75 kHz to 80 kHz are obtained from the pair of the piezoelectric elements 9a and 9b as the objective values and the objective values are assigned to x1 and x2 to calculate a value of Y. This enables presence or absence of a fine micro crack to be detected according to the value of Y exceeding 0 (Y>0) or being less than 0 (Y<0).

Figure 19A:
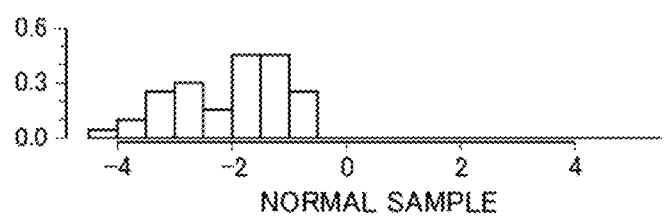
FIG. 19A is a graph classifying the error and normal samples at values obtained by a discriminant in discriminant analysis.
Figure 19B:
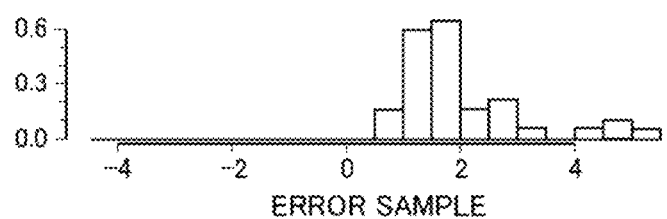
FIG. 19B is a table illustrating discriminant results of the error and normal samples determined as error and normal products.
Figure 20A:
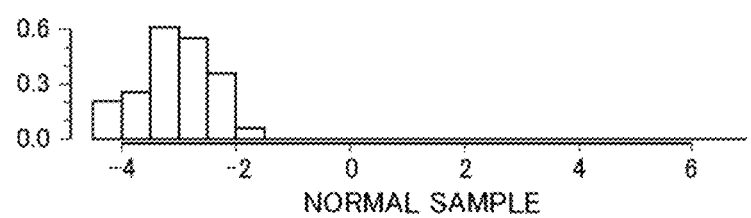
FIG. 20A is a graph classifying the error and normal samples at values obtained by a discriminant in discriminant analysis.
Figure 20B:
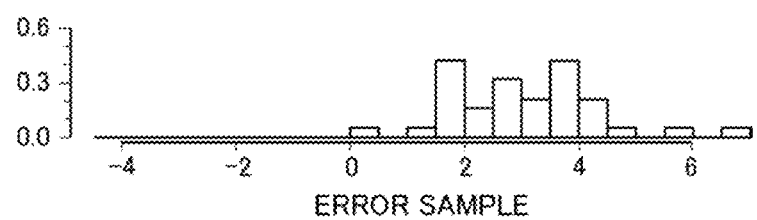
FIG. 20B is a table illustrating discriminant results of the error and normal samples determined as error and normal products.

FIGS. 19A and 19B illustrates discriminant result using three parameters. FIGS. 20A and 20B illustrates discriminant result using other three parameters.

For the discriminant analysis of FIGS. 19A and 19B, three parameters are the frequency value in the phase characteristic in the frequency range F4 of 55 kHz to 65 kHz, the frequency value in the phase characteristic in the frequency range F5 of 65 kHz to 80 kHz, and the area value in the gain characteristic in the frequency range F6 of 75 kHz to 80 kHz.

For the discriminant analysis of FIGS. 20A and 20B, three parameters are the peak value in the gain characteristic in the frequency range F4 of 55 kHz to 65 kHz, the peak value in the gain characteristic in the frequency range F6 of 75 kHz to 80 kHz, and the frequency value in the phase characteristic in the frequency range F4.

In FIGS. 19 and 20, the discriminant analyses determine a sample having a value of Y that is less than 0 (Y<0) in the discriminant or the discriminant function Y=a0+a1*x1+a2*x2+a3*x3 as a normal sample and a sample having a value of Y that exceeds 0 (Y>0) as an error sample. In the discriminant function, a0 is a constant term, a1, a2 and a3 are coefficients, and x1, x2 and x3 are the parameters. The constant term a0 and the coefficients a1 to a3 can be obtained in the same way as the commonly-known method. With the discriminant analyses, the error samples are correctly determined as error products and the normal samples as normal products.

Thus, the discriminant functions for the discriminant analyses of FIGS. 19 and 20 are used as the discriminants with three parameters to detect presence or absence of a fine micro crack.

Parameters and coefficients that enable a fine micro crack to be detected should be used suitable for a specification of a piezoelectric actuator and therefore should be set through discriminant analysis.

Main effects of the embodiment will be explained.

The crack detecting method includes applying voltage to the first piezoelectric element 9a of the pair of the piezoelectric elements 9a and 9b that are united with each other and are deformable integrally, to cause deformation in the first piezoelectric element 9a (voltage applying step S1), forcibly deforming the second piezoelectric element 9b of the pair of the piezoelectric elements 9a and 9b according to the deformation of the first piezoelectric element 9a, to generate voltage from the second piezoelectric element 9b (forcibly deforming step S2), finding the transfer function G(s) of the pair of the piezoelectric elements 9a and 9b based on the value of the applied voltage to the first piezoelectric element 9a and the value of the generated voltage from the second piezoelectric element 9b (function finding step S3), and detecting presence or absence of a crack in one or both of the pair of the piezoelectric elements 9a and 9b based on an objective value obtained from the found transfer function G(s) (crack detecting step S4).

The crack detecting method according to the embodiment, therefore, applies the voltage to only the first piezoelectric element 9a to generate voltage from the second piezoelectric element 9b. Then, the transfer function G(s) is found using the values of the applied voltage and the generated voltage. The found transfer function G(s) provides the objective value that enables a crack to be surely detected even if the crack is a fine micro crack.

Namely, the crack detecting method surely detects a crack in one or both of the pair of the piezoelectric element 9a and 9b regardless of size of the crack.

Further, the crack detecting method in the crack detecting step S4 simply compares the objective value with the reference value to easily detect a fine micro crack or evaluates the objective value using the discriminant to detect a fine micro crack with high accuracy.

The reference value is the value obtained from the transfer function found in advance based on at least one error sample of a pair of piezoelectric elements in which one or both first and second piezoelectric elements are cracked or at least one normal sample of a pair of piezoelectric elements in which both first and second piezoelectric elements are not cracked. Accordingly, the embodiment easily sets the reference value.

The discriminant is the discriminant function obtained by discriminant analysis of error values and normal values, the error values obtained from transfer functions found in advance based on plural error samples each being a pair of piezoelectric elements in which one or both first and second piezoelectric elements are cracked and the normal values obtained from transfer functions found in advance based on plural normal samples each being a pair of piezoelectric elements in which both first and second piezoelectric elements are not cracked. Accordingly, the embodiment easily sets the discriminant.

The crack detecting apparatus 1 according to the embodiment includes the power source 3 electrically connected to the first piezoelectric element 9a of the pair of the piezoelectric elements 9a and 9b that are united with each other and are deformable integrally to apply voltage to the first piezoelectric element 9a and cause the first piezoelectric element 9a to deform, the voltage measuring device 5 electrically connected to the second piezoelectric element 9b of the pair of the piezoelectric elements 9a and 9b to measure voltage generated from the second piezoelectric element 9b that is forcibly deformed according to the deformation of the first piezoelectric element 9a, and the crack detector 7 electrically connected to the power source 3 and the voltage measuring device 5. The crack detector 7 obtains from the power source 3 a value of the applied voltage to the first piezoelectric element 9a and from the voltage measuring device 5 a value of the measured voltage, finds the transfer function G(s) of the pair of the piezoelectric elements 9a and 9b based on the values of the applied voltage and the measured voltage, and detects presence or absence of a crack in one or both of the pair of the piezoelectric elements 9a and 9b based on the objective value obtained from the found transfer function G(s).

Accordingly, the crack detecting apparatus 1 easily and simply realizes the crack detecting method to precisely detect a fine micro crack.

What is claimed is:

1. A method of detecting a crack in piezoelectric elements, comprising:
    applying voltage to a first piezoelectric element of a pair of piezoelectric elements that are united with each other and are deformable integrally, to cause deformation in the first piezoelectric element;
    forcibly deforming a second piezoelectric element of the pair of the piezoelectric elements according to the deformation of the first piezoelectric element, to generate voltage from the second piezoelectric element;
    finding a transfer function of the pair of the piezoelectric elements based on a value of the applied voltage to the first piezoelectric element and a value of the generated voltage from the second piezoelectric element; and
    detecting presence or absence of a crack in one or both of the pair of the piezoelectric elements by comparing an objective value obtained from the found transfer function with a reference value, wherein the reference value is predetermined by:
        finding, in advance, transfer functions from plural error samples, each being a pair of piezoelectric elements in which one or both of first and second piezoelectric elements are cracked, and plural normal samples, each being pair of piezoelectric elements in which both of first and second piezoelectric elements are not cracked;
        defining a range for a group of corresponding peaks in waveforms of the transfer functions of the error samples and the normal samples, the group of the corresponding peaks involving deviation in waveform between the error samples and the normal samples and the range defined for the group not including adjacent groups of other corresponding peaks;
        specifying a parameter from among parameters being obtained from the waveforms of the transfer functions of the error samples and the normal samples and relating to corresponding peaks in at least one range defined in the defining step, the specified parameter being a parameter in which a value range of the error samples does not overlap a value range of the normal samples; and
        setting a border between the value ranges of the error samples and the normal samples of the specified parameter in said at least one range as the reference value to be compared with the objective value found for the specified parameter in the detecting step.

2. The method according to claim 1, wherein
    the pair of piezoelectric elements have respective first ends attached to a stationary member and respective second ends attached to a movable member,
    the applying step displaces the movable member according to the deformation of the first piezoelectric element, and
    the deforming step forcibly deforms the second piezoelectric element by the displaced movable member to generate the voltage from the second piezoelectric element.

3. The method according to claim 1, wherein
    the transfer function is a frequency transfer function,
    the parameters relating to the corresponding peaks are a peak value, an area value and a frequency value of the corresponding peaks in a gain characteristic and a phase characteristic of a waveform of the frequency transfer function, and
    said range is a frequency range.

4. A method of detecting a crack in piezoelectric elements, comprising:
    applying voltage to a first piezoelectric element of a pair of piezoelectric elements that are united with each other and are deformable integrally, to cause deformation in the first piezoelectric element;
    forcibly deforming a second piezoelectric element of the pair of the piezoelectric elements according to the deformation of the first piezoelectric element, to generate voltage from the second piezoelectric element;
    finding a transfer function of the pair of the piezoelectric elements based on a value of the applied voltage to the first piezoelectric element and a value of the generated voltage from the second piezoelectric element; and
    detecting presence or absence of a crack in one or both of the pair of the piezoelectric elements by evaluating an objective value obtained from the found transfer function using a discriminant, wherein the discriminant is predetermined by:
        finding, in advance, transfer functions from plural error samples, each being a pair of piezoelectric elements in which one or both of first and second piezoelectric elements are cracked, and plural normal samples, each being a pair of piezoelectric elements in which both of first and second piezoelectric elements are not cracked;
        defining a range for a group of corresponding peaks in waveforms of the transfer functions of the error samples and the normal samples, the group of the corresponding peaks involving deviation in waveform between the error samples and the normal samples and the range defined for the group not including adjacent groups of other corresponding peaks;
        specifying a combination of two or more parameters from among parameters being obtained from the waveforms of the transfer functions of the error samples and the normal samples and relating to corresponding peaks in each range set in the defining step by performing round-robin discriminant analysis to all of the parameters obtained from the waveforms of the transfer functions of the error samples and the normal samples, the specified combination of the parameters discriminating between the error samples and the normal samples in the discriminant analysis; and
        finding the discriminant according to the specified combination of the parameters to be used to evaluate the objective value found for the specified combination of the parameters in the detecting step.

5. The method according to claim 4, wherein
    the pair of piezoelectric elements have respective first ends attached to a stationary member and respective second ends attached to a movable member,
    the applying step displaces the movable member according to the deformation of the first piezoelectric element, and
    the deforming step forcibly deforms the second piezoelectric element by the displaced movable member to generate the voltage from the second piezoelectric element.

6. The method according to claim 4, wherein
the transfer function is a frequency transfer function,
the parameters relating to the corresponding peaks are a peak value, an area value and a frequency value of the corresponding peaks in a gain characteristic and a phase characteristic of a waveform of the frequency transfer function, and
said range is a frequency range.

* * * * *